United States Patent
DeSimone et al.

(10) Patent No.: US 7,943,079 B2
(45) Date of Patent: May 17, 2011

(54) METHODS OF MAKING ORTHODONTIC APPLIANCES

(75) Inventors: Joseph M. DeSimone, Chapel Hill, NC (US); Robert E. Tricca, Danville, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 12/620,826

(22) Filed: Nov. 18, 2009

(65) Prior Publication Data

US 2010/0065976 A1    Mar. 18, 2010

Related U.S. Application Data

(62) Division of application No. 10/963,252, filed on Oct. 12, 2004, now Pat. No. 7,641,828.

(51) Int. Cl.
*B29C 59/00* (2006.01)
(52) U.S. Cl. .......... 264/346; 264/16; 264/129; 264/292; 264/235; 264/571; 433/6; 433/18
(58) Field of Classification Search .............. 264/16, 264/129, 292, 235, 346, 571; 433/18, 6
See application file for complete search history.

(56) References Cited

U.S. PATENT DOCUMENTS

| | | | |
|---|---|---|---|
| 5,372,796 | A | 12/1994 | Wellinghoff |
| 5,405,921 | A | 4/1995 | Muschiatti et al. |
| 5,670,583 | A | 9/1997 | Weillinghoff |
| 5,975,893 | A | 11/1999 | Chishti et al. |
| 2005/0100853 | A1* | 5/2005 | Tadros et al. ............ 433/6 |

FOREIGN PATENT DOCUMENTS

| | | |
|---|---|---|
| WO | WO 00/32131 | 6/2000 |
| WO | WO 03/003935 | 1/2003 |
| WO | WO 03/094256 | 11/2003 |

OTHER PUBLICATIONS

International Search Report and Written Opinion of the International Searching Authority corresponding to PCT/US2005/027666, mailed Dec. 6, 2005.

* cited by examiner

*Primary Examiner* — Matthew J Daniels
*Assistant Examiner* — Russell J Kemmerle, III
(74) *Attorney, Agent, or Firm* — Myers Bigel Sibley & Sajovec, P.A.

(57) ABSTRACT

Methods of making a removable dental positioning appliance include forming a sheet of transparent crystalline polymeric material into a shell having cavities shaped to receive and reposition teeth from a first orientation to a successive orientation. The polymeric material may then be annealed at a temperature above its glass transition temperature or cured if a curable material to enhance characteristics of the polymeric material. The polymeric material may be coated with a second transparent material.

85 Claims, 2 Drawing Sheets

METHODS OF MAKING ORTHODONTIC APPLIANCES

RELATED APPLICATION

This application is a divisional application of U.S. patent application Ser. No. 10/963,252 filed Oct. 12, 2004 now U.S Pat. No. 7,641,828 which is incorporated herein by reference in its entirety.

FIELD OF THE INVENTION

The present invention relates generally to orthodontics and, more particularly, to orthodontic appliances for incrementally moving teeth from an initial tooth arrangement to a final tooth arrangement.

BACKGROUND OF THE INVENTION

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces include a variety of appliances such as brackets, bands, archwires, ligatures, and O-rings. After braces are bonded to the teeth, periodic meetings with an orthodontist are typically required to adjust the braces. This may involve installing different archwires with different force-inducing properties and/or may include replacing or tightening existing ligatures. Between meetings, the patient may be required to wear supplementary appliances, such as elastic bands or headgear, to supply additional or extraoral forces.

Although conventional braces can be effective, their use often is a tedious and time consuming process that requires many visits to an orthodontist. Moreover, from a patient's perspective, braces are unsightly and uncomfortable. Consequently, alternative orthodontic treatments have developed. A particularly promising approach relies on the use of elastic positioning appliances for realigning teeth. Such appliances comprise a thin shell of elastic material that generally conforms to a patient's teeth, but that is slightly out of alignment with the patient's initial tooth configuration. Placement of the elastic positioner over the teeth applies controlled forces in specific locations to gradually move the teeth into the new configuration. Repetition of this process with successive appliances having different configurations eventually moves a patient's teeth through a series of intermediate configurations to a final desired configuration. A full description of exemplary elastic polymeric positioning appliances and methods of using same are described in U.S. Pat. No. 5,975, 893, commonly assigned to the assignee of the instant invention and which is incorporated herein by reference in its entirety.

Polymeric positioning appliances, such as those described in the '893 patent, are advantageous over conventional braces in that they are easy to use and they are generally transparent, providing an improved cosmetic appearance. Unfortunately, polymeric materials currently utilized in the production of these positioning appliances may undergo stress relaxation and creep, which can seriously degrade the ability of an appliance to reposition teeth as desired. In addition, polymeric materials currently utilized may be susceptible to degradation as a result of exposure to saliva and other chemicals present within a patient's mouth.

SUMMARY OF THE INVENTION

According to embodiments of the present invention, a method of making a removable dental positioning appliance includes forming a sheet of transparent crystalline polymeric material into a shell having cavities shaped to receive and reposition teeth from a first orientation to a successive orientation and then annealing the shell at a temperature above the glass transition temperature of the transparent crystalline polymeric material. Annealing is performed at a temperature and time sufficient to cause the annealed transparent crystalline polymeric material to preferably have a tensile strength at yield of greater than 6,000 psi, preferably have an elongation at yield of greater than 4%, preferably have an elongation at break of greater than 80%, preferably have a tensile modulus greater than 200,000 psi, preferably have a flexural modulus greater than 200,000 psi, preferably have stress relaxation over time of not more than 50%, and preferably have a transmissivity of light between 400 nm and 800 nm greater than 75%.

According to embodiments of the present invention, a method of making a removable dental positioning appliance includes forming a sheet of transparent curable polymeric material into a shell having cavities shaped to receive and reposition teeth from a first orientation to a successive orientation and then curing the polymeric material. When cured, the transparent polymeric material preferably has a tensile strength at yield of greater than 6,000 psi, preferably has an elongation at yield of greater than 4%, preferably has an elongation at break of greater than 80%, preferably has a tensile modulus greater than 200,000 psi, preferably has a flexural modulus greater than 200,000 psi, preferably has stress relaxation over time of not more than 50%, and preferably has a transmissivity of light between 400 nm and 800 nm greater than 75%. Even more preferably, the cured transparent polymeric material has a tensile strength at yield of greater than 8,800 psi, preferably has an elongation at yield of greater than 5%, preferably has an elongation at break of greater than 100%, preferably has a tensile modulus greater than 300,000 psi, preferably has a flexural modulus greater than 330,000 psi, preferably has stress relaxation over time of not more than 30%, and preferably has a transmissivity of light between 400 nm and 800 nm greater than 80%.

According to embodiments of the present invention, a method of making a removable dental positioning appliance includes forming a sheet of transparent curable polymeric material into a shell having cavities shaped to receive and reposition teeth from a first orientation to a successive orientation and then coating the polymeric shell with a second transparent material. If the coating is a curable material, the shell and coating are then subjected to curing operations to cure the coating material. The coated appliance preferably has a tensile strength at yield of greater than 6,000 psi, preferably has an elongation at yield of greater than 4%, preferably has an elongation at break of greater than 80%, preferably has a tensile modulus greater than 200,000 psi, preferably has a flexural modulus greater than 200,000 psi, preferably has stress relaxation over time of not more than 50%, and preferably has a transmissivity of light between 400 nm and 800 nm greater than 75%. Even more preferably, the coated appliance has a tensile strength at yield of greater than 8,800 psi, preferably has an elongation at yield of greater than 5%, preferably has an elongation at break of greater than 100%, preferably has a tensile modulus greater than 300,000 psi, preferably has a flexural modulus greater than 330,000 psi, preferably has stress relaxation over time of not more than 30%, and preferably has a transmissivity of light between 400 nm and 800 nm greater than 80%.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. As used herein, the term "and/or" includes any and all combinations of one or more of the associated listed items.

Figure 1:
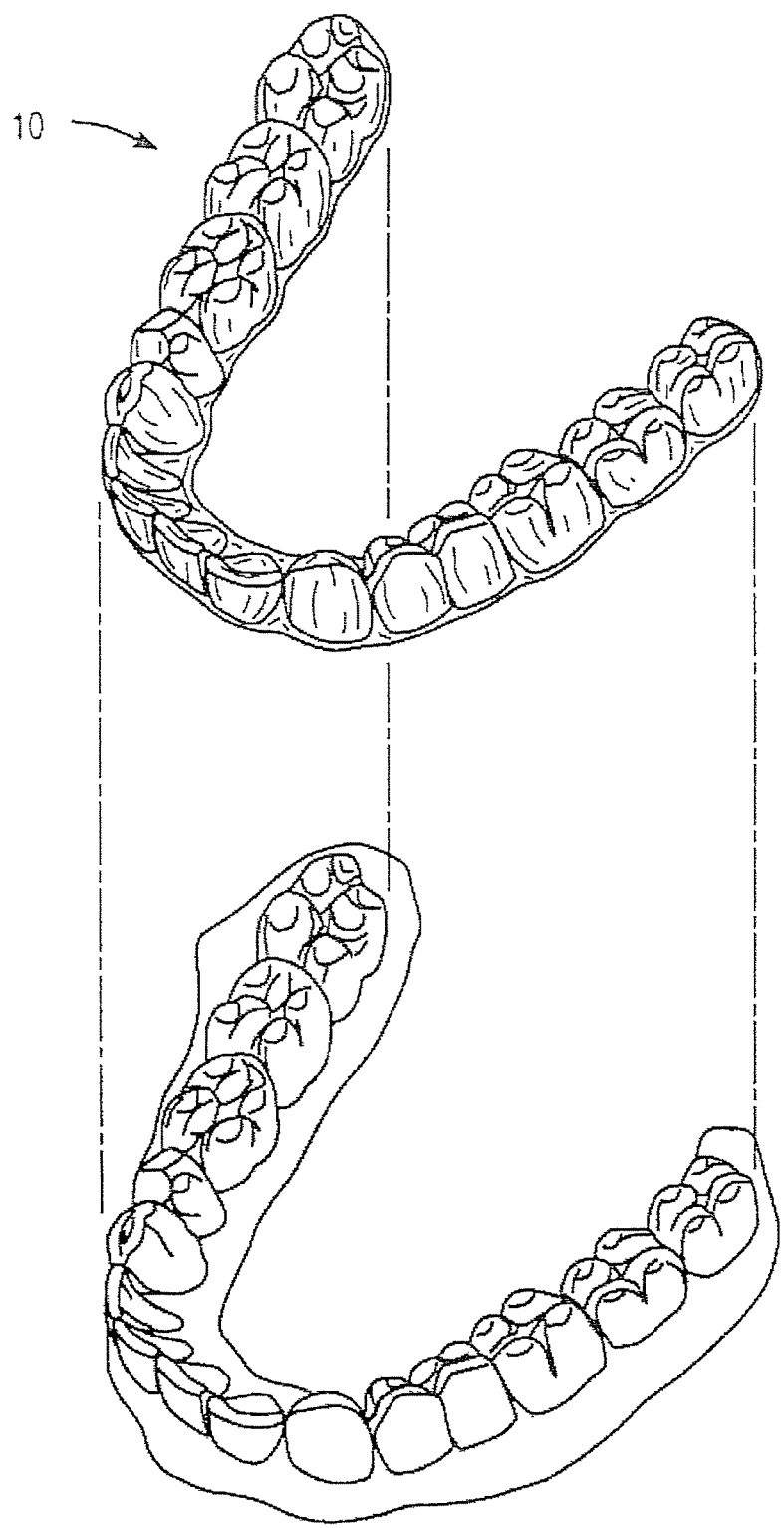
FIG. 1 is a perspective view of a removable dental positioning appliance that may be formed by various methods in accordance with embodiments of the present invention.

U.S. Pat. No. 5,975,893 describes methods and systems for repositioning a patient's teeth from an initial tooth arrangement to a final tooth arrangement by placing a series of polymeric shell appliances in the patient's mouth. The appliances are not affixed to the patient's teeth and the patient may place and replace the appliances at any time during the procedure. The first appliance of the series has a geometry selected to reposition the teeth from the initial tooth arrangement to a first intermediate arrangement. After the first intermediate arrangement is approached or achieved, one or more additional (intermediate) appliances are successively placed on the teeth, where such additional appliances have geometries selected to progressively reposition teeth from the first intermediate arrangement through successive intermediate arrangement(s). The treatment is finished by placing a final appliance in the patient's mouth, where the final appliance has a geometry selected to progressively reposition teeth from the last intermediate arrangement to the final tooth arrangement. FIG. 1 illustrates an exemplary dental positioning appliance 10 described in the '893 patent.

The polymeric shells of dental positioning appliances for a patient, such as illustrated in FIG. 1, are produced by initially obtaining a digital data set (IDDS) representing an initial tooth arrangement. The IDDS may be obtained in a variety of ways. For example, the patient's teeth may be scanned or imaged using well known technology, such as X-rays, three-dimensional x-rays, computer-aided tomographic images or data sets, magnetic resonance images, etc. The IDDS is then digitally manipulated via a computer to produce a final tooth arrangement, which is incorporated into a final digital data set (FDDS). Based on both the IDDS and the FDDS, a plurality of intermediate digital data sets (INTDDS's) are generated to correspond to successive intermediate tooth arrangements that correspond to tooth movement from the initial tooth arrangement to the final tooth arrangement.

Using the intermediate and final data sets, positive tooth models of a patient's teeth corresponding to each of the intermediate and final data sets are produced. After the positive models are prepared, a conventional pressure or vacuum molding machine may be used to produce the polymer shells of dental positioning appliances from a thermoformable material. The molding machine produces each of the appliances directly from a positive tooth model. The appliances are marked in some manner, typically by sequential numbering directly on the appliances or on tags, pouches, or other items which are affixed to or which enclose each appliance, to indicate their order of use.

Figure 2:
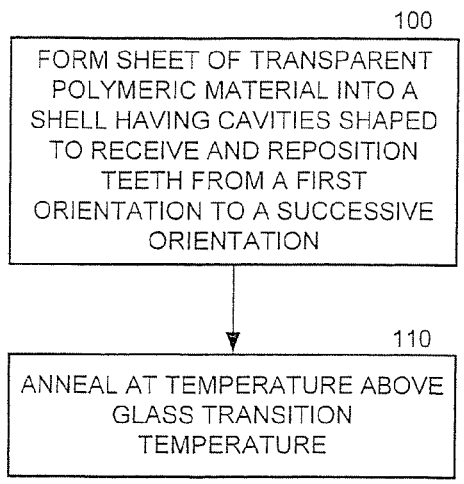
FIGS. 2-4 are flow charts illustrating methods of making a removable dental positioning appliance according to embodiments of the present invention

According to embodiments of the present invention, methods of making removable dental positioning appliances, such as illustrated in FIG. 1, with improved material properties are provided. Referring initially to FIG. 2, a method of making a removable dental positioning appliance according to an embodiment of the present invention includes forming a sheet of transparent crystalline polymeric material into a shell having cavities shaped to receive and reposition teeth from a first orientation to a successive orientation (Block 100) and then annealing the shell at a temperature above the glass transition temperature of the transparent crystalline polymeric material (Block 110). Annealing is performed at a temperature and time sufficient to cause the annealed transparent crystalline polymeric material to preferably have a tensile strength at yield of greater than 6,000 psi, preferably have an elongation at yield of greater than 4%, preferably have an elongation at break of greater than 80%, preferably have a tensile modulus greater than 200,000 psi, preferably have a flexural modulus greater than 200,000 psi, preferably have stress relaxation over time of not more than 50%, and preferably have a transmissivity of light between 400 nm and 800 nm greater than 75%.

Even more preferably, annealing is performed at a temperature and time sufficient to cause the annealed transparent crystalline polymeric material to preferably have a tensile strength at yield of greater than 8,800 psi, preferably have an elongation at yield of greater than 5%, preferably have an elongation at break of greater than 100%, preferably have a tensile modulus greater than 300,000 psi, preferably have a flexural modulus greater than 330,000 psi, preferably have stress relaxation over time of not more than 30%, and preferably have a transmissivity of light between 400 nm and 800 nm greater than 80%.

Preferably, the annealing temperature is between the glass transition temperature and melting temperature of the transparent crystalline polymeric material (i.e., $T_g < T_{anneal} < T_m$). However, various annealing temperatures may be utilized. Annealing is preferably performed for at least about one minute. However, annealing may be performed for various time periods in accordance with embodiments of the present invention. Annealing times and temperatures will vary depending on the material of the shell and the coating material, as would be understood by those skilled in the art.

According to embodiments of the present invention, annealing may be performed in the presence of a nucleating agent disposed on or within the transparent crystalline polymeric material. As known to those skilled in the art, nucleating agents are chemical substances which, when incorporated in polymer materials, form nuclei for the growth of crystals in the polymer melt. For example, in certain polymers, a higher degree of crystallinity and more uniform crystalline structure may be obtained by adding a nucleating agent.

According to embodiments of the present invention, annealing may be performed selectively. The term "selective annealing" is used herein to indicate that a physical property of the transparent crystalline polymeric material can be accurately controlled and modified to specific parameters via annealing. Selective annealing can allow for customization of a removable dental appliance. For example, crystallinity can be selectively increased, which can decrease the optical transparency, in portions of the shell of a removable dental appliance that are not visible when worn by a user. Other, visible portions may have less crystallinity and, thereby, more transparency. Selective annealing can occur by heating only certain portions of the shell. Other properties of the transparent crystalline polymeric material which may be controlled via selective annealing include, but are not limited to, tensile strength at yield, elongation at yield, elongation at break, tensile modulus, flexural modulus, stress relaxation, etc.

Annealing polymeric materials can also lead to densification of the amorphous phase, which is often referred to as physical aging. Such densification of amorphous phases can lead to an increase in modulus of the device.

Annealing may be performed by only heating selected portions of the shell of a removable dental positioning appliance. For example, a light source or laser may be utilized to heat selected portions of the shell of a removable dental positioning appliance. According to other embodiments of the present invention, annealing may be performed by adding chemical crosslink agents only to certain areas of the transparent crystalline polymeric material of the shell of a removable dental positioning appliance.

According to other embodiments of the present invention, annealing may be performed by selectively subjecting the transparent crystalline polymeric material to irradiation, such as e-beam irradiation, UV-visible irradiation and/or gamma irradiation.

According to embodiments of the present invention, exemplary transparent crystalline polymeric materials include, but are not limited to, liquid crystalline polymeric materials, styrenics, and ion-containing polymers. Applicants have discovered that removable dental positioning appliances formed from liquid crystalline polymers, styrenics, and ion-containing polymers that are annealed to have one or more of the above-listed characteristics are less susceptible to stress relaxation and creep than conventional dental positioning appliances. Moreover, Applicants have discovered that removable dental positioning appliances formed from liquid crystalline polymers, styrenics, and ion-containing polymers that are annealed to have one or more of the above-listed characteristics are less susceptible to degradation caused by exposure to saliva and other chemicals in a patient's mouth. Annealing significantly reduces internal stress levels, which increases chemical resistance of the material.

Exemplary liquid crystalline polymeric materials according to embodiments of the present invention include, but are not limited to branched liquid crystalline polymers and polyarylates. Crystallizable polyester compositions are also suitable and are described in U.S. Pat. No. 5,405,921, which is incorporated herein by reference in its entirety. Crystallizable polyesters utilized in accordance with embodiments of the present invention preferably have a glass transition temperature of at least 50° C. and/or a melting point of at least 150° C. In terms of intrinsic viscosity (IV), crystallizable polyesters should have an IV of at least about 0.5 as measured in a 1:1 by weight solution of methylene chloride and trifluoroacetic acid. The polyester base resin preferably is present in an amount of about 79-99 wt % based upon the total weight of the formulations used in the practice of this invention. A single polyester material need not be used. Copolyesters and blends may be used.

To obtain a clear product based upon crystallized polyester, the polymer must be oriented prior to the onset of crystallization. The orientation of the polyester results in the formation of elongated crystallites. Elongated crystallites allow incident light to pass without substantial diffraction, which results in a clear, transparent product.

Other exemplary crystalline polymeric materials that may be utilized in accordance with embodiments of the present invention include polyethylene terephthalate (PET) (e.g., DuPont Teijin Films Melinex®) and polyethylene naphthalate (PEN) films (e.g., DuPont Teijin Films Teonex®. PET and PEN films have an inherent advantage over amorphous polymer films because PET and PEN are both semi-crystalline and biaxially oriented polymers. Moreover, PET and PEN films will typically absorb approximately 1,400 ppm of moisture at equilibrium.

According to other embodiments of the present invention, dental positioning appliances may be formed from PVC modified with Elvaloy® ketone ethylene ester (DuPont, Wilmington, Del.). Elvaloy® modified PVC has been found to be more resistant to creep than PVC and HDPE.

Exemplary styrenic polymeric materials according to embodiments of the present invention include, but are not limited to polystyrene (PS), expanded polystyrene (EPS), acrylonitrile-butadiene-styrene (ABS), styrene-acrylonitrile (SAN), styrene block copolymers (SBC), unsaturated polyester resins (uPES), styrene butadiene rubber (SBR), and styrene butadiene latex (SBL). Styrenic polymeric materials are rigid, transparent, tough, resistant to grease, stress cracking and crazing. Styrenic polymeric materials are also easily processed and resistant to food stains. Styrenic polymeric materials are available from a variety of sources including Bayer AG, Leverkusen, Germany, The Dow Chemical Company, Midland, Mich., and PolyOne Corporation, Avon Lake, OH.

Exemplary ion-containing polymeric materials include, but are not limited to, Surlyn® brand resin (DuPont, Inc., Wilmington, Del.). Other important commercial ionomers include Nafion® brand polymers (Ion Power, Inc., Bear, Del.). Nafion® brand polymers are sulfonated tetrafluoroethylene ionomer and sulfonated polystyrene. Ionomers have significantly better properties than the un-ionized precursor because the ionic groups phase separate into ion-rich domains.

Other exemplary polymeric materials that can be formed and annealed, in accordance with embodiments of the present invention, include transparent polymeric materials with high glass transition temperatures (e.g., at least 155° C.). Exemplary transparent polymeric materials having high glass transition temperatures include, but are not limited to norbornene-containing polymers, metallocene, metal-catalyzed polyolefins, cyclo-olefins, poly(methyl-1-pentene), amorphous aromatic resins, poly(benzophenone)s, polyamides, thermoplastic polyurethanes, polyetherimides, poly(arylene ether ketone)s, polysulfones, biphenyl endcapped poly (acrylene ether) polymers, polycarbonates, polyesters, poly (estercarbonate)s, cellulosics, and acrylics.

Other exemplary transparent materials having high glass transition temperatures include Paramax® (Mississippi Polymer Technologies) and polyamides. Paramax® is a very hard polymer with a low coefficient of thermal expansion, and a high refractive index. Paramax® can be molded extruded and cast from solution and produces clear alloys with other engineering thermoplastics. Paramax® is miscible with polycarbonate and polysulfone. Paramax® has a high surface hardness which provides excellent scratch resistance. Other exemplary transparent materials having high glass transition temperatures include SUNTUF®, PALSUN® and PAL-TUF™ polycarbonate sheets, PALGLAS® acrylic sheets; PAL-G™ co-polyester sheets, and PALRUF® PVC sheets, all available from Suntuf, Inc. Kutztown, Pa.

According to embodiments of the present invention, transparent acrylic and polycarbonate materials having high glass transition temperatures are processed with a supermicrocellular foaming technique developed by Wright Materials Research Co., Beavercreek, OH. This technique utilizes biphenyl endcapped poly(acrylene ether) polymers.

Other exemplary transparent materials having high glass transition temperatures include Trogamid® brand transparent polyamides (Degussa AG, Marl, Germany). Trogamid® brand transparent polyamides are permanently transparent, have high chemical resistance, and have a low tendency to creep.

Other exemplary materials that can be formed and annealed, in accordance with embodiments of the present invention, include laminates and/or blends of transparent polymeric materials. Exemplary blends of transparent polymers include, but are not limited to, polyester blends such as polybutylene terephthalate (PBT) blends and polyethylene terephthalate (PET) blends. Polyester blends, in general, have high strength and rigidity. Exemplary transparent laminates include, but are not limited to, polycarbonate-based laminates, acrylic-based laminates, Paramax® brand polymers, polycarbonates, and polysulfone.

Figure 3:
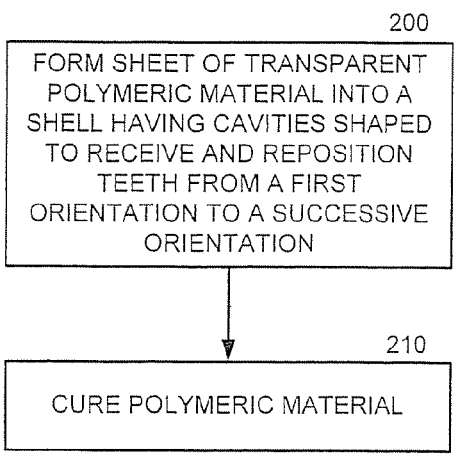

Referring to FIG. 3, a method of making a removable dental positioning appliance according to an embodiment of the present invention includes forming a sheet of transparent curable polymeric material into a shell having cavities shaped to receive and reposition teeth from a first orientation to a successive orientation (Block 200) and then curing the polymeric material (Block 210). When cured, the transparent polymeric material preferably has a tensile strength at yield of greater than 6,000 psi, preferably has an elongation at yield of greater than 4%, preferably has an elongation at break of greater than 80%, preferably has a tensile modulus greater than 200,000 psi, preferably has a flexural modulus greater than 200,000 psi, preferably has stress relaxation over time of not more than 50%, and preferably has a transmissivity of light between 400 nm and 800 nm greater than 75%. Even more preferably, the cured transparent polymeric material preferably has a tensile strength at yield of greater than 8,800 psi, preferably has an elongation at yield of greater than 5%, preferably has an elongation at break of greater than 100%, preferably has a tensile modulus greater than 300,000 psi, preferably has a flexural modulus greater than 330,000 psi, preferably has stress relaxation over time of not more than 30%, and preferably has a transmissivity of light between 400 nm and 800 nm greater than 80%.

Exemplary curable transparent polymeric materials that may be utilized in accordance with embodiments of the present invention include, but are not limited to, epoxies, sol-gel coatings, polyurethanes, polyureas, and unsaturated polyesters.

According to embodiments of the present invention, curing the transparent polymeric material may be performed by irradiating the transparent polymeric material with ionizing electromagnetic radiation such as gamma radiation, ultraviolet radiation, microwave radiation, electron beam radiation, x-ray radiation, etc. To facilitate curing with ionizing electromagnetic radiation, the transparent polymeric material may contain various additives including, but not limited to, radiation stabilizers and antioxidants which act to protect the polymeric material from damage caused by the radiation. Such additives are referred to as "antirads" and function either as reactants, combining readily with radiation-generated free radicals in the polymer material, or as energy absorbers, preventing the radiation from interacting with the polymer itself.

In addition to curing, ionizing radiation may be utilized to enhance the material characteristics of polymers used in dental positioning appliances in accordance with embodiments of the present invention. Many important physical and chemical properties of polymers can be modified with ionizing radiation including, but not limited to, molecular weight, polymer chain length, entanglement, polydispersity, branching, pendant functionality, and chain termination. Radiation, such as gamma and electron beam irradiation, may also be utilized to sterilize the polymeric material of dental positioning appliances, according to embodiments of the present invention.

Embodiments of the present invention are not limited to curing with ionizing electromagnetic radiation. Curing may also be performed via the addition of heat (i.e., thermal curing), as would be understood by those skilled in the art.

Applicants have discovered that removable dental positioning appliances coated with materials as described above are less susceptible to stress relaxation and creep than conventional dental positioning appliances. Moreover, Applicants have discovered that removable dental positioning appliances coated with materials as described above are less susceptible to degradation caused by exposure to saliva and other chemicals in a patient's mouth.

Figure 4:
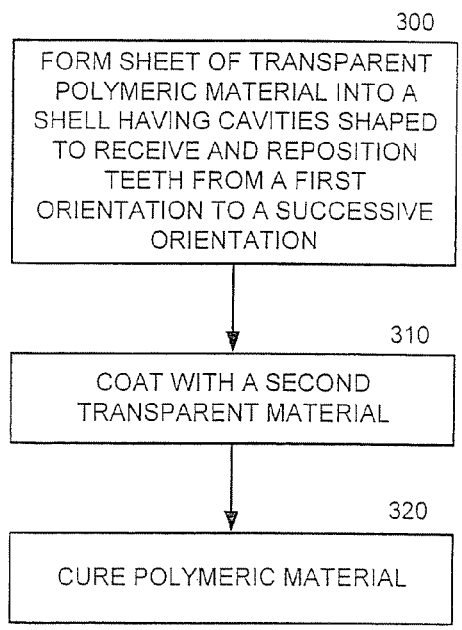

Referring to FIG. 4, a method of making a removable dental positioning appliance according to an embodiment of the present invention includes forming a sheet of transparent curable polymeric material into a shell having cavities shaped to receive and reposition teeth from a first orientation to a successive orientation (Block 300) and then coating the polymeric shell with a second transparent material (Block 310). If the coating is a curable material, the shell and coating are then subjected to curing operations (Block 320) to cure the coating material. According to embodiments of the present invention, curing operations may be performed by irradiating the transparent polymeric material with ionizing electromagnetic radiation such as gamma radiation, ultraviolet radiation, microwave radiation, electron beam radiation and x-ray radiation. To facilitate curing with ionizing electromagnetic radiation, the transparent polymeric material may contain various additives including, but not limited to, radiation stabilizers and antioxidants. Embodiments of the present invention are not limited to curing with ionizing electromagnetic radiation. Curing may also be performed via the addition of heat (i.e., thermal curing), as would be understood by those skilled in the art.

A coated polymeric shell of a removable dental positioning appliance, according to embodiments of the present invention, preferably has a tensile strength at yield of greater than 6,000 psi, preferably has an elongation at yield of greater than 4%, preferably has an elongation at break of greater than 80%, preferably has a tensile modulus greater than 200,000 psi, preferably has a flexural modulus greater than 200,000 psi, preferably has stress relaxation over time of not more than 50%, and preferably has a transmissivity of light between 400 nm and 800 nm greater than 75%. Even more preferably, the coated polymeric shell has a tensile strength at yield of greater than 8,800 psi, preferably has an elongation at yield of greater than 5%, preferably has an elongation at break of greater than 100%, preferably has a tensile modulus greater than 300,000 psi, preferably has a flexural modulus greater than 330,000 psi, preferably has stress relaxation over time of not more than 30%, and preferably has a transmissivity of light between 400 nm and 800 nm greater than 80%.

According to embodiments of the present invention, the first transparent material used to form the shell may include polyurethanes, liquid crystalline polymeric materials, styrenics, ion-containing polymers, polymeric laminates and polymeric blends. Exemplary liquid crystalline polymeric materials include, but are not limited to, polyesters, polyamides, polycarbonates, polyolefins, poly(cycloolefins), branched liquid crystalline polymers and polyarylates.

Exemplary styrenic polymeric materials according to embodiments of the present invention include, but are not limited to polystyrene (PS), expanded polystyrene (EPS), acrylonitrile-butadiene-styrene (ABS), styrene-acrylonitrile (SAN), styrene block copolymers (SBC), unsaturated polyester resins (uPES), styrene butadiene rubber (SBR), and styrene butadiene latex (SBL). Exemplary ion-containing polymeric materials include, but are not limited to, Surlyn® brand resin and Nafion® brand polymers.

According to embodiments of the present invention, the first transparent material used to form the shell may have a glass transition temperature of at least 100° C.

According to embodiments of the present invention, the first transparent material used to form the shell may include filler material including, but not limited to, inorganic materials and/or organic materials. Exemplary inorganic filler materials include, but are not limited to, metal oxides, oxygenates, carbonates, halides, and sulfates. Exemplary organic filler materials include, but are not limited to, waxes and oligomeric polymers.

According to embodiments of the present invention, the first transparent material used to form the shell may include ultra-high molecular weight polymers.

According to embodiments of the present invention, the first transparent material used to form the shell may include uniaxially oriented polymers and/or bi-axially oriented polymers.

According to embodiments of the present invention, the first transparent material used to form the shell may include Barix® brand vapor barrier film.

According to embodiments of the present invention, the second transparent material may be a curable polymeric material. Exemplary curable coating materials, according to embodiments of the present invention, include, but are not limited to, epoxies, acrylics, alkyds, acrylate resins which incorporate corrosion protective fillers and other materials, multifunctional acrylates (MFMs), acrylated oligomers, or monofunctional diluent monomers, solvent free powder coatings, sol-gel coatings, polyurethanes, polyureas, and unsaturated polyesters. Various photoinitiators may be utilized including, but not limited to, free radical, acid, cationic, etc. Curing the second transparent material may include irradiating the coating with ionizing electromagnetic radiation, such as gamma radiation, ultraviolet radiation, microwave radiation, electron beam radiation, x-ray radiation, etc. The second transparent material may include radiation stabilizers and/or antioxidants.

According to embodiments of the present invention, the second transparent material may be durable, non-curable polymeric material. Exemplary non-curable polymeric materials include, but are not limited to, acrylics, silicone, inorganic-containing materials, polycarbonates, and polyurethanes.

According to embodiments of the present invention, the second transparent material has a glass transition temperature or a melting point of at least 150° C.

According to embodiments of the present invention, the second transparent material includes Barix® brand vapor barrier film.

According to embodiments of the present invention, the second transparent material includes advanced thermoplastic composite (ATC) material.

According to embodiments of the present invention, the second transparent material includes ISOPLAST® 2530 polyurethane resin (The Dow Chemical Company, Midland, Mich.). ISOPLAST® 2530 polyurethane resin is a clear amorphous polymer with excellent chemical resistance, high heat, low moisture sensitivity, toughness, and dimensional stability.

According to embodiments of the present invention, the second transparent material may contain a material, such as silicon dioxide, to improve abrasion resistance of the removable dental positioning appliance. According to embodiments of the present invention, the second transparent material may contain a material, such as silicon dioxide, that serves as a barrier to harmful substances (e.g., water vapor, oxygen, etc.). According to embodiments of the present invention, the second transparent material may contain a material that avoids the formation of fog. Exemplary antifog materials include, but are not limited to, silicon oxides.

In each of the above-described embodiments, the transparent polymeric material of the dental positioning appliance may include uniaxially oriented polymers and/or bi-axially oriented polymers.

In each of the above-described embodiments, the transparent polymeric material of the dental positioning appliance may include filler material including, but not limited to, inorganic materials and/or organic materials. Exemplary inorganic filler materials include, but are not limited to, metal oxides, oxygenates, carbonates, halides, and sulfates. U.S. Pat. Nos. 5,372,796 and 5,670,583, each of which is incorporated herein by reference in its entirety, describe metal oxide clusters and ceramers (polymer-ceramic composites). According to embodiments of the present invention, alloys of polymers with ceramic particles of diameter much smaller than the wavelength of visible light can be used to produce a material with a high refractive index, and that are scratch and corrosion resistant. Exemplary organic filler materials include, but are not limited to, waxes and oligomeric polymers.

In each of the above-described embodiments, the transparent polymeric material of the dental positioning appliance may include additives, such as ultra-high molecular weight polymers. An exemplary ultra-high molecular weight polymer that may be utilized in accordance with embodiments of the present invention is ultra-high molecular weight polyethylene (UHMWPE), available from Cambridge Polymer Group, Boston, Mass. The wear properties of ultra-high molecular weight polymers, as well as other types of polymers, can be enhanced with radiation, such as electron beam and gamma irradiation.

The invention claimed is:
1. A method of making a removable dental positioning appliance, comprising:
forming a sheet of transparent polymeric material into a shell having cavities shaped to receive and reposition teeth from a first orientation to a successive orientation, wherein the transparent polymeric material comprises inorganic filler material selected from the group consisting of metal oxides, oxygenates, carbonates, halides, and sulfates; and annealing the shell at a temperature above a glass transition temperature of the transparent polymeric material.

2. The method of claim 1, wherein the transparent polymeric material comprises amorphous polymeric material and wherein annealing the shell comprises heating the amorphous polymeric material to a temperature above a glass transition temperature of the amorphous polymeric material for a period of time sufficient to selectively densify the amorphous polymeric material.

3. The method of claim 1, wherein the transparent polymeric material comprises amorphous polymeric material and wherein annealing the shell comprises heating the amorphous polymeric material to a temperature above a glass transition temperature of the amorphous polymeric material for a period of time sufficient to selectively crystallize the amorphous polymeric material.

4. The method of claim 1, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively decrease stress in the semi-crystalline polymeric material.

5. The method of claim 1, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively enhance crystallization of the semi-crystalline polymeric material.

6. The method of claim 1, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively densify the semi-crystalline polymeric material.

7. The method of claim 1, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively increase or decrease the modulus of the semi-crystalline polymeric material.

8. The method of claim 1, wherein the shell is annealed such that the transparent polymeric material has a tensile strength at yield of greater than 6,000 psi, an elongation at yield of greater than 4%, an elongation at break of greater than 80%, a tensile modulus greater than 200,000 psi, a flexural modulus greater than 200,000 psi, stress relaxation over time of not more than 50%, and a transmissivity of light between 400 nm and 800 nm greater than 75%.

9. The method of claim 1, wherein the shell is annealed such that the transparent polymeric material has a tensile strength at yield of greater than 8,800 psi, an elongation at yield of greater than 5%, an elongation at break of greater than 100%, a tensile modulus greater than 300,000 psi, a flexural modulus greater than 330,000 psi, stress relaxation over time of not more than 30%, and a transmissivity of light between 400 nm and 800 nm greater than 80%.

10. The method of claim 1, wherein annealing is performed at a temperature between the glass transition temperature of the transparent polymeric material and the melting temperature of the transparent polymeric material.

11. The method of claim 1, wherein annealing is performed for at least about one minute.

12. The method of claim 1, wherein the transparent polymeric material comprises styrenic polymer material.

13. The method of claim 1, wherein the transparent polymeric material comprises ultra-high molecular weight polymers.

14. The method of claim 1, wherein the transparent polymeric material comprises styrenic polymeric material selected from the group consisting of acrylonitrile-butadiene-styrene (ABS), styrene-acrylonitrile (SAN), and styrene block copolymers (SBC).

15. The method of claim 1, wherein the transparent polymeric material comprises ion-containing polymers.

16. The method of claim 1, wherein annealing is performed only on a selected portion of the shell.

17. A method of making a removable dental positioning appliance, comprising:

forming a sheet of transparent polymeric material into a shell having cavities shaped to receive and reposition teeth from a first orientation to a successive orientation, wherein the transparent polymeric material comprises organic filler material selected from the group consisting of waxes and oligomeric polymers; and annealing the shell at a temperature above a glass transition temperature of the transparent polymeric material.

18. The method of claim 17, wherein the transparent polymeric material comprises amorphous polymeric material and wherein annealing the shell comprises heating the amorphous polymeric material to a temperature above a glass transition temperature of the amorphous polymeric material for a period of time sufficient to selectively densify the amorphous polymeric material.

19. The method of claim 17, wherein the transparent polymeric material comprises amorphous polymeric material and wherein annealing the shell comprises heating the amorphous polymeric material to a temperature above a glass transition temperature of the amorphous polymeric material for a period of time sufficient to selectively crystallize the amorphous polymeric material.

20. The method of claim 17, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively decrease stress in the semi-crystalline polymeric material.

21. The method of claim 17, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively enhance crystallization of the semi-crystalline polymeric material.

22. The method of claim 17, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively densify the semi-crystalline polymeric material.

23. The method of claim 17, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively increase or decrease the modulus of the semi-crystalline polymeric material.

24. The method of claim 17, wherein the shell is annealed such that the transparent polymeric material has a tensile strength at yield of greater than 6,000 psi, an elongation at yield of greater than 4%, an elongation at break of greater than 80%, a tensile modulus greater than 200,000 psi, a flexural modulus greater than 200,000 psi, stress relaxation over time of not more than 50%, and a transmissivity of light between 400 nm and 800 nm greater than 75%.

25. The method of claim 17, wherein the shell is annealed such that the transparent polymeric material has a tensile strength at yield of greater than 8,800 psi, an elongation at yield of greater than 5%, an elongation at break of greater than 100%, a tensile modulus greater than 300,000 psi, a flexural modulus greater than 330,000 psi, stress relaxation over time of not more than 30%, and a transmissivity of light between 400 nm and 800 nm greater than 80%.

26. The method of claim 17, wherein annealing is performed at a temperature between the glass transition temperature of the transparent polymeric material and the melting temperature of the transparent polymeric material.

27. The method of claim 17, wherein annealing is performed for at least about one minute.

28. The method of claim 17, wherein the transparent polymeric material comprises styrenic polymeric material.

29. The method of claim 17, wherein the transparent polymeric material comprises ultra-high molecular weight polymers.

30. The method of claim 17, wherein the transparent polymeric material comprises styrenic polymeric material selected from the group consisting of acrylonitrile-butadiene-styrene (ABS), styrene-acrylonitrile (SAN), and styrene block copolymers (SBC).

31. The method of claim 17, wherein the transparent polymeric material comprises ion-containing polymers.

32. The method of claim 17, wherein annealing is performed only on a selected portion of the shell.

33. A method of making a removable dental positioning appliance, comprising:
forming a sheet of transparent polymeric material into a shell having cavities shaped to receive and reposition teeth from a first orientation to a successive orientation, wherein the transparent polymeric material comprises ultra-high molecular weight polymers; and
annealing the shell at a temperature above a glass transition temperature of the transparent polymeric material.

34. The method of claim 33, wherein the transparent polymeric material comprises amorphous polymeric material and wherein annealing the shell comprises heating the amorphous polymeric material to a temperature above a glass transition temperature of the amorphous polymeric material for a period of time sufficient to selectively densify the amorphous polymeric material.

35. The method of claim 33, wherein the transparent polymeric material comprises amorphous polymeric material and wherein annealing the shell comprises heating the amorphous polymeric material to a temperature above a glass transition temperature of the amorphous polymeric material for a period of time sufficient to selectively crystallize the amorphous polymeric material.

36. The method of claim 33 wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively decrease stress in the semi-crystalline polymeric material.

37. The method of claim 33, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively enhance crystallization of the semi-crystalline polymeric material.

38. The method of claim 33, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively densify the semi-crystalline polymeric material.

39. The method of claim 33, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively increase or decrease the modulus of the semi-crystalline polymeric material.

40. The method of claim 33, wherein the shell is annealed such that the transparent polymeric material has a tensile strength at yield of greater than 6,000 psi, an elongation at yield of greater than 4%, an elongation at break of greater than 80%, a tensile modulus greater than 200,000 psi, a flexural modulus greater than 200,000 psi, stress relaxation over time of not more than 50%, and a transmissivity of light between 400 nm and 800 nm greater than 75%.

41. The method of claim 33, wherein the shell is annealed such that the transparent polymeric material has a tensile strength at yield of greater than 8,800 psi, an elongation at yield of greater than 5%, an elongation at break of greater than 100%, a tensile modulus greater than 300,000 psi, a flexural modulus greater than 330,000 psi, stress relaxation over time of not more than 30%, and a transmissivity of light between 400 nm and 800 nm greater than 80%.

42. The method of claim 33, wherein annealing is performed at a temperature between the glass transition temperature of the transparent polymeric material and the melting temperature of the transparent polymeric material.

43. The method of claim 33, wherein annealing is performed for at least about one minute.

44. The method of claim 33, wherein the transparent polymeric material comprises styrenic polymeric material.

45. The method of claim 33, wherein the transparent polymeric material comprises filler material selected from the group consisting of inorganic materials and organic materials.

46. The method of claim 33, wherein the transparent polymeric material comprises inorganic filler material selected from the group consisting of metal oxides, oxygenates, carbonates, halides, and sulfates.

47. The method of claim 33, wherein the transparent polymeric material comprises organic filler material selected from the group consisting of waxes and oligomeric polymers.

48. The method of claim 33, wherein the transparent polymeric material comprises styrenic polymeric material selected from the group consisting of acrylonitrile-butadiene-styrene (ABS), styrene-acrylonitrile (SAN), and styrene block copolymers (SBC).

49. The method of claim 33, wherein the transparent polymeric material comprises ion-containing polymeric resin.

50. The method of claim 34, wherein annealing is performed only on a selected portion of the shell.

51. A method of making a removable dental positioning appliance, comprising:
forming a sheet of transparent polymeric material into a shell having cavities shaped to receive and reposition teeth from a first orientation to a successive orientation, wherein the transparent polymeric material comprises styrenic polymeric material; and
annealing the shell at a temperature above a glass transition temperature of the transparent polymeric material.

52. The method of claim 51, wherein the transparent polymeric material comprises styrenic polymeric material selected from the group consisting of acrylonitrile-butadiene-styrene (ABS), styrene-acrylonitrile (SAN), and styrene block copolymers (SBC).

53. The method of claim 51, wherein the transparent polymeric material comprises amorphous polymeric material and wherein annealing the shell comprises heating the amorphous polymeric material to a temperature above a glass transition temperature of the amorphous polymeric material for a period of time sufficient to selectively densify the amorphous polymeric material.

54. The method of claim 51, wherein the transparent polymeric material comprises amorphous polymeric material and wherein annealing the shell comprises heating the amorphous polymeric material to a temperature above a glass transition temperature of the amorphous polymeric material for a period of time sufficient to selectively crystallize the amorphous polymeric material.

55. The method of claim 51, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively decrease stress in the semi-crystalline polymeric material.

56. The method of claim 51, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively enhance crystallization of the semi-crystalline polymeric material.

57. The method of claim 51, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively densify the semi-crystalline polymeric material.

58. The method of claim 51, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively increase or decrease the modulus of the semi-crystalline polymeric material.

59. The method of claim 51, wherein the shell is annealed such that the transparent polymeric material has a tensile strength at yield of greater than 6,000 psi, an elongation at yield of greater than 4%, an elongation at break of greater than 80%, a tensile modulus greater than 200,000 psi, a flexural modulus greater than 200,000 psi, stress relaxation over time of not more than 50%, and a transmissivity of light between 400 nm and 800 nm greater than 75%.

60. The method of claim 51, wherein the shell is annealed such that the transparent polymeric material has a tensile strength at yield of greater than 8,800 psi, an elongation at yield of greater than 5%, an elongation at break of greater than 100%, a tensile modulus greater than 300,000 psi, a flexural modulus greater than 330,000 psi, stress relaxation over time of not more than 30%, and a transmissivity of light between 400 nm and 800 nm greater than 80%.

61. The method of claim 51, wherein annealing is performed at a temperature between the glass transition temperature of the transparent polymeric material and the melting temperature of the transparent polymeric material.

62. The method of claim 51, wherein annealing is performed for at least about one minute.

63. The method of claim 51, wherein the transparent polymeric material comprises filler material selected from the group consisting of inorganic materials and organic materials.

64. The method of claim 51, wherein the transparent polymeric material comprises inorganic filler material selected from the group consisting of metal oxides, oxygenates, carbonates, halides, and sulfates.

65. The method of claim 51, wherein the transparent polymeric material comprises organic filler material selected from the group consisting of waxes and oligomeric polymers.

66. The method of claim 51, wherein the transparent polymeric material comprises ultra-high molecular weight polymers.

67. The method of claim 51, wherein the transparent polymeric material comprises ion-containing polymeric resin.

68. The method of claim 51, wherein annealing is performed only on a selected portion of the shell.

69. A method of making a removable dental positioning appliance, comprising:
forming a sheet of transparent polymeric material into a shell having cavities shaped to receive and reposition teeth from a first orientation to a successive orientation, wherein the transparent polymeric material comprises ion-containing polymers; and
annealing the shell at a temperature above a glass transition temperature of the transparent polymeric material.

70. The method of claim 69, wherein the transparent polymeric material comprises styrenic polymeric material selected from the group consisting of acrylonitrile-butadiene-styrene (ABS), styrene-acrylonitrile (SAN), and styrene block copolymers (SBC).

71. The method of claim 69, wherein the transparent polymeric material comprises amorphous polymeric material and wherein annealing the shell comprises heating the amorphous polymeric material to a temperature above a glass transition temperature of the amorphous polymeric material for a period of time sufficient to selectively densify the amorphous polymeric material.

72. The method of claim 69, wherein the transparent polymeric material comprises amorphous polymeric material and wherein annealing the shell comprises heating the amorphous polymeric material to a temperature above a glass transition temperature of the amorphous polymeric material for a period of time sufficient to selectively crystallize the amorphous polymeric material.

73. The method of claim 69, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively decrease stress in the semi-crystalline polymeric material.

74. The method of claim 69, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively enhance crystallization of the semi-crystalline polymeric material.

75. The method of claim 69, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively densify the semi-crystalline polymeric material.

76. The method of claim 69, wherein the transparent polymeric material comprises semi-crystalline polymeric material and wherein annealing the shell comprises heating the semi-crystalline polymeric material to a temperature above a glass transition temperature of the semi-crystalline polymeric material for a period of time sufficient to selectively increase or decrease the modulus of the semi-crystalline polymeric material.

77. The method of claim 69, wherein the shell is annealed such that the transparent polymeric material has a tensile strength at yield of greater than 6,000 psi, an elongation at yield of greater than 4%, an elongation at break of greater than 80%, a tensile modulus greater than 200,000 psi, a flexural modulus greater than 200,000 psi, stress relaxation over time of not more than 50%, and a transmissivity of light between 400 nm and 800 nm greater than 75%.

78. The method of claim 69, wherein the shell is annealed such that the transparent polymeric material has a tensile strength at yield of greater than 8,800 psi, an elongation at yield of greater than 5%, an elongation at break of greater than 100%, a tensile modulus greater than 300,000 psi, a flexural modulus greater than 330,000 psi, stress relaxation over time of not more than 30%, and a transmissivity of light between 400 nm and 800 nm greater than 80%.

79. The method of claim 69, wherein annealing is performed at a temperature between the glass transition temperature of the transparent polymeric material and the melting temperature of the transparent polymeric material.

80. The method of claim 69, wherein annealing is performed for at least about one minute.

81. The method of claim 69, wherein the transparent polymeric material comprises filler material selected from the group consisting of inorganic materials and organic materials.

82. The method of claim 69, wherein the transparent polymeric material comprises inorganic filler material selected from the group consisting of metal oxides, oxygenates, carbonates, halides, and sulfates.

83. The method of claim 69, wherein the transparent polymeric material comprises organic filler material selected from the group consisting of waxes and oligomeric polymers.

84. The method of claim 69, wherein the transparent polymeric material comprises ultra-high molecular weight polymers.

85. The method of claim 69, wherein annealing is performed only on a selected portion of the shell.

* * * * *